United States Patent
Wasserman et al.

(10) Patent No.: US 11,097,101 B2
(45) Date of Patent: Aug. 24, 2021

(54) TEMPERATURE MEASUREMENT IN ARRAYS FOR DELIVERING TTFIELDS

(71) Applicant: Novocure Limited, St. Helier (JE)

(72) Inventors: Yoram Wasserman, Haifa (IL); Michael Krinitsky, Beersheva (IL); Mikhail Shtotland, Beer Sheva (IL); Victor Kaikov, Atlit (IL)

(73) Assignee: Novocure GmbH, Root (CH)

( * ) Notice: Subject to any disclaimer, the term of this patent is extended or adjusted under 35 U.S.C. 154(b) by 258 days.

(21) Appl. No.: 15/674,984

(22) Filed: Aug. 11, 2017

(65) Prior Publication Data
US 2018/0050200 A1    Feb. 22, 2018

Related U.S. Application Data

(60) Provisional application No. 62/376,885, filed on Aug. 18, 2016.

(51) Int. Cl.
| | |
|---|---|
| *A61N 1/40* | (2006.01) |
| *A61N 1/36* | (2006.01) |
| *A61B 18/14* | (2006.01) |
| *A61N 1/04* | (2006.01) |
| *A61K 41/00* | (2020.01) |
| *A61N 1/06* | (2006.01) |

(Continued)

(52) U.S. Cl.
CPC .......... *A61N 1/36002* (2017.08); *A61B 18/14* (2013.01); *A61K 41/0052* (2013.01); *A61N 1/0408* (2013.01); *A61N 1/0476* (2013.01); *A61N 1/0492* (2013.01); *A61N 1/06* (2013.01); *A61N 1/32* (2013.01); *A61N 1/3603* (2017.08); *A61N 1/40* (2013.01); *A61B 2018/00648* (2013.01); *A61N 1/18* (2013.01)

(58) Field of Classification Search
None
See application file for complete search history.

(56) References Cited

U.S. PATENT DOCUMENTS

| | | | |
|---|---|---|---|
| 4,688,573 A | * | 8/1987 | Alt ........................ A61N 1/3655 607/21 |
| 5,239,999 A | | 8/1993 | Imran |

(Continued)

FOREIGN PATENT DOCUMENTS

WO    2009/065042 A2    5/2009

OTHER PUBLICATIONS

International Search Report and Written Opinion for International Application No. PCT/IB2017/054922 dated Nov. 20, 2017.

*Primary Examiner* — Kennedy Schaetzle
(74) *Attorney, Agent, or Firm* — Potomac Law Group, PLLC (57) ABSTRACT

TTFields therapy is a proven approach for treating tumors using electric fields. This application describes systems and methods for measuring the temperature at the electrode elements of the transducer arrays that are used to apply the TTFields to a subject. A distal circuit is positioned adjacent to each transducer array, and the distal circuit interfaces with temperature sensors in the transducer array to obtain temperature readings. Those temperature readings are transmitted to a central hub. In some embodiments, temperature measurements from all of the distal circuits occur simultaneously.

20 Claims, 8 Drawing Sheets

(51) Int. Cl.
  *A61N 1/32* (2006.01)
  *A61B 18/00* (2006.01)
  *A61N 1/18* (2006.01)

(56) References Cited

U.S. PATENT DOCUMENTS

| | | |
|---|---|---|
| 8,706,261 B2 | 4/2014 | Palti |
| 2008/0027507 A1* | 1/2008 | Bijelic ................. A61N 1/0452 607/48 |
| 2008/0281311 A1 | 11/2008 | Dunning et al. |
| 2009/0076366 A1 | 3/2009 | Palti |
| 2009/0264809 A1* | 10/2009 | Sen .................... A61K 48/0075 604/20 |
| 2014/0330268 A1 | 11/2014 | Palti et al. |
| 2016/0081580 A1* | 3/2016 | Bergelin ................ A61B 5/445 600/554 |
| 2017/0246450 A1* | 8/2017 | Liu ...................... A61N 1/0456 |

\* cited by examiner

TEMPERATURE MEASUREMENT IN ARRAYS FOR DELIVERING TTFIELDS

CROSS REFERENCE TO RELATED APPLICATIONS

This Application claims the benefit of U.S. Provisional Application 62/376,885, filed Aug. 8, 2016, which is incorporated herein by reference in its entirety.

BACKGROUND

TTFields therapy is a proven approach for treating tumors. In the prior art Optune® system for delivering TTFields, the TTFields are delivered to patients via four transducer arrays placed on the patient's skin in close proximity to a tumor. The transducer arrays are arranged in two pairs, and each transducer array is connected via a multi-wire cable to a field generator. The field generator (a) sends an AC current through one pair of arrays during a first period of time; then (b) sends an AC current through the other pair of arrays during a second period of time; then repeats steps (a) and (b) for the duration of the treatment.

Each transducer array is configured as a set of capacitively coupled electrode elements (about 2 cm in diameter) that are interconnected via flex wires. Each electrode element includes a ceramic disk that is sandwiched between a layer of an electrically conductive medical gel and an adhesive tape. When placing the arrays on the patient, the medical gel adheres to the contours of the patient's skin and ensures good electric contact of the device with the body. The adhesive tape holds the entire array in place on the patient as the patient goes about their daily activities.

The amplitude of the alternating current that is delivered via the transducer arrays is controlled so that skin temperature (as measured on the skin below the transducer arrays) does not exceed a safety threshold of 41 degrees Celsius. The temperature measurements on the patient's skin are obtained using thermistors placed beneath some of the disks of the transducer arrays. In the existing Optune® system, each array includes 8 thermistors, with one thermistor positioned beneath a respective disk in the array. (Note that most arrays include more than 8 disks, in which case the temperature measurements are only performed beneath a sub-set of the disks within the array).

The thermistors in each of the four arrays are connected via long wires to an electronic device called the "cable box" where the temperature from all 32 thermistors (4 arrays×8 thermistors per array) is measured and analog-to-digital converted into digital values for each thermistor. These measurements are then transmitted from the cable box to the field generator via an additional two wires that facilitate two-way digital serial communications between the cable box and the field generator. The controller in the field generator uses the temperature measurements to control the current to be delivered via each pair of arrays in order to maintain temperatures below 41 degrees Celsius on the patient's skin. The current itself is delivered to each array via an additional wire (i.e., one wire for each array) that runs from the field generator through the cable box to the array.

In the existing Optune® system there are four long 10-wire cables (each of which runs between a respective array and the cable box) and one 8-wire spiral cord that runs between the field generator and the cable box. Each of the 10-wire cables has 8 wires for carrying signals from the 8 thermistors, 1 wire for the common of all 8 thermistors, plus 1 wire for providing the TTFields signal to the array. The 8-wire spiral cord has 1 wire for power to the cable box (Vcc), 1 wire for ground to the cable box, 2 wires for data communication (to send the temperature readings to the field generator), plus 4 wires for TTFields signal (i.e., one for each of the four arrays).

SUMMARY OF THE INVENTION

One aspect of the invention is directed to a first apparatus for use together with a AC signal generator for imposing electric fields through a target region in a subject's body. This first apparatus includes a plurality of capacitively coupled electrode elements configured for placement against the subject's body. A substrate is configured to hold the plurality of electrode elements against the subject's body. A plurality of temperature sensors are positioned to sense temperatures at respective ones of the plurality of electrode elements. The first apparatus also includes an analog multiplexer having an analog output and a plurality of selectable analog inputs, wherein each of the plurality of analog inputs is operatively connected to a respective one of the plurality of temperature sensors. It also includes an analog to digital converter configured to digitize signals arriving from the analog output, and a controller. The controller is configured to (a) sequentially select each of the plurality of analog inputs, (b) sequentially obtain, from the analog to digital converter, a plurality of temperature readings, each of the plurality of temperature readings corresponding to a respective one of the plurality of temperature sensors, and (c) transmit digital data corresponding to the plurality of temperature readings. The first apparatus also includes a cable having a proximal end and a distal end. The cable includes (i) a conductor that permits AC current to flow between the proximal end of the cable and the distal end of the cable and (ii) a data path configured to carry the transmitted digital data from the distal end of the cable to the proximal end of the cable. The plurality of electrode elements is electrically connected to the conductor. The analog multiplexer, the analog to digital converter, and the controller are mounted to the substrate or to the distal end of the cable.

In some embodiments of the first apparatus, the plurality of temperature sensors comprises a plurality of thermistors.

In some embodiments of the first apparatus, the cable has a length of 25 cm or less. In some embodiments of the first apparatus, the cable has a length of 10 cm or less.

Some embodiments of the first apparatus further include a connector disposed between the controller and the distal end of the cable. In some of these embodiments, the analog multiplexer, the analog to digital converter, and the controller are mounted to the substrate.

Some embodiments of the first apparatus further include a connector disposed between the plurality of temperature sensors and the plurality of analog inputs. In some of these embodiments, the analog multiplexer, the analog to digital converter, and the controller are mounted to the distal end of the cable.

Some embodiments of the first apparatus further include a precision resistor. In these embodiments, the analog multiplexer has an additional selectable analog input that is operatively connected to the precision resistor. In these embodiments, the controller is further configured to (d) select the additional analog input, (e) obtain, from the analog to digital converter, an additional reading that corresponds to the precision resistor, and (f) transmit digital data corresponding to the additional reading.

Some embodiments of the first apparatus further include a precision resistor. In these embodiments, the analog multiplexer has an additional selectable analog input that is operatively connected to the precision resistor. In these embodiments, the controller is further configured to (d) select the additional analog input, (e) obtain, from the analog to digital converter, an additional reading that corresponds to the precision resistor, and (f) calibrate, based on the additional reading, each of the plurality of temperature readings prior to transmission of the corresponding digital data.

In some embodiments of the first apparatus, the cable uses a single conductor to provide the data path that carries the transmitted digital data from the distal end of the cable to the proximal end of the cable.

In some embodiments of the first apparatus, the cable uses a single conductor to provide the data path that carries the transmitted digital data from the distal end of the cable to the proximal end of the cable, a single conductor for providing power to the controller, and a single conductor for ground.

In some embodiments of the first apparatus, energy arriving via the conductor in the cable is used to power the controller.

Another aspect of the invention is directed to a second apparatus for use together with an AC signal generator for imposing electric fields through a target region in a subject's body. This second apparatus includes a hub configured to accept digital data corresponding to first, second, third, and fourth pluralities of temperature readings and output digital data corresponding to the first, second, third, and fourth pluralities of temperature readings to the AC signal generator. The hub includes first, second, third, and fourth conductors configured to route current from the AC signal generator to positions that are located distally beyond the hub.

This second apparatus also includes first, second, third, and fourth pluralities of capacitively coupled electrode elements configured for placement against the subject's body at first, second, third, and fourth positions, respectively. This second apparatus also includes first, second, third, and fourth substrates configured to hold the corresponding pluralities of electrode elements against the subject's body at first, second, third, and fourth positions. This second apparatus also includes first, second, third, and fourth pluralities of temperature sensors positioned to sense the temperatures at respective ones of the first, second, third, and fourth pluralities of electrode elements. This second apparatus also includes first, second, third, and fourth analog multiplexers having first, second, third, and fourth analog outputs, respectively. These multiplexers have first, second, third, and fourth pluralities of selectable analog inputs, respectively. Each analog input within the first, second, third, and fourth pluralities of analog inputs is operatively connected to a respective temperature sensor within the first, second, third, and fourth pluralities of temperature sensors. This second apparatus also includes first, second, third, and fourth analog to digital converters configured to digitize signals arriving from the first, second, third, and fourth analog outputs, respectively. This second apparatus also includes first, second, third, and fourth controllers. These controllers are configured to (a) sequentially select each input within the first, second, third, and fourth pluralities of analog inputs, respectively; (b) sequentially obtain, from the first, second, third, and fourth analog to digital converters, respectively, first, second, third, and fourth pluralities of temperature readings—each reading within the first, second, third, and fourth pluralities of temperature readings corresponding to a respective temperature sensor within the first, second, third, and fourth pluralities of temperature sensors; and (c) transmit first, second, third, and fourth digital data corresponding to the first, second, third, and fourth pluralities of temperature readings to the hub. This second apparatus also includes first, second, third, and fourth cables arranged to route current arriving via the first, second, third, and fourth conductors in the hub to the first, second, third, and fourth pluralities of electrode elements, respectively; and to route the first, second, third, and fourth digital data from the first, second, third, and fourth controller, respectively, to the hub.

In some embodiments of the second apparatus, the first, second, third, and fourth controllers are synchronized so that the first, second, third, and fourth pluralities of temperature readings are obtained simultaneously.

In some embodiments of the second apparatus, the first, second, third, and fourth controllers are synchronized so that at least a portion of the first, second, third, and fourth pluralities of temperature readings are obtained simultaneously.

Some embodiments of the second apparatus further include first, second, third, and fourth precision resistors. In these embodiments, each of the analog multiplexers has an additional selectable analog input that is operatively connected to a respective precision resistor. The first, second, third, and fourth controllers are further configured to (d) select the respective additional analog input, (e) obtain, from the respective analog to digital converter, first, second, third, and fourth additional readings that correspond to the respective precision resistor, and (f) transmit digital data corresponding to the first, second, third, and fourth additional readings to the hub. In some of these embodiments, the hub is further configured to calibrate, based on the first, second, third, and fourth additional readings, each temperature reading within the first, second, third, and fourth pluralities of temperature readings.

Some embodiments of the second apparatus further include first, second, third, and fourth precision resistors. In these embodiments, each of the analog multiplexers has an additional selectable analog input that is operatively connected to a respective precision resistor. The first, second, third, and fourth controllers are further configured to (d) select the respective additional analog input, (e) obtain, from the respective analog to digital converter, first, second, third, and fourth additional readings that correspond to the respective precision resistor, and (f) calibrate, based on the first, second, third, and fourth additional readings, respectively, each reading within the first, second, third, and fourth pluralities of temperature readings prior to transmission of the corresponding digital data to the hub, Some embodiments of the second apparatus further include first, second, third, and fourth connectors disposed, respectively, between the first, second, third, and fourth, controllers and the hub.

Some embodiments of the second apparatus further include first, second, third, and fourth connectors disposed, respectively, between the first, second, third, and fourth pluralities of temperature sensors and the first, second, third, and fourth pluralities of analog inputs, respectively.

In some embodiments of the second apparatus, each of the first, second, third, and fourth cables uses a single conductor for routing current arriving via the first, second, third, and fourth conductors in the hub to the first, second, third, and fourth pluralities of electrode elements, respectively. In these embodiments, each of the first, second, third, and fourth cables also has a single conductor for transferring digital data between the first, second, third, and fourth controllers and the hub, respectively.

In some embodiments of the second apparatus, each of the first, second, third, and fourth cables uses a single conductor for routing current arriving via the first, second, third, and fourth conductors in the hub to the first, second, third, and fourth pluralities of electrode elements, respectively. In these embodiments, each of the first, second, third, and fourth cables also has a single conductor for transferring digital data between the first, second, third, and fourth controllers and the hub, respectively; a single conductor for providing power to the respective controller; and a single conductor for a respective ground.

In some embodiments of the second apparatus, energy arriving via the first, second, third, and fourth conductors in the hub is used to power the first, second, third, and fourth controllers, respectively.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
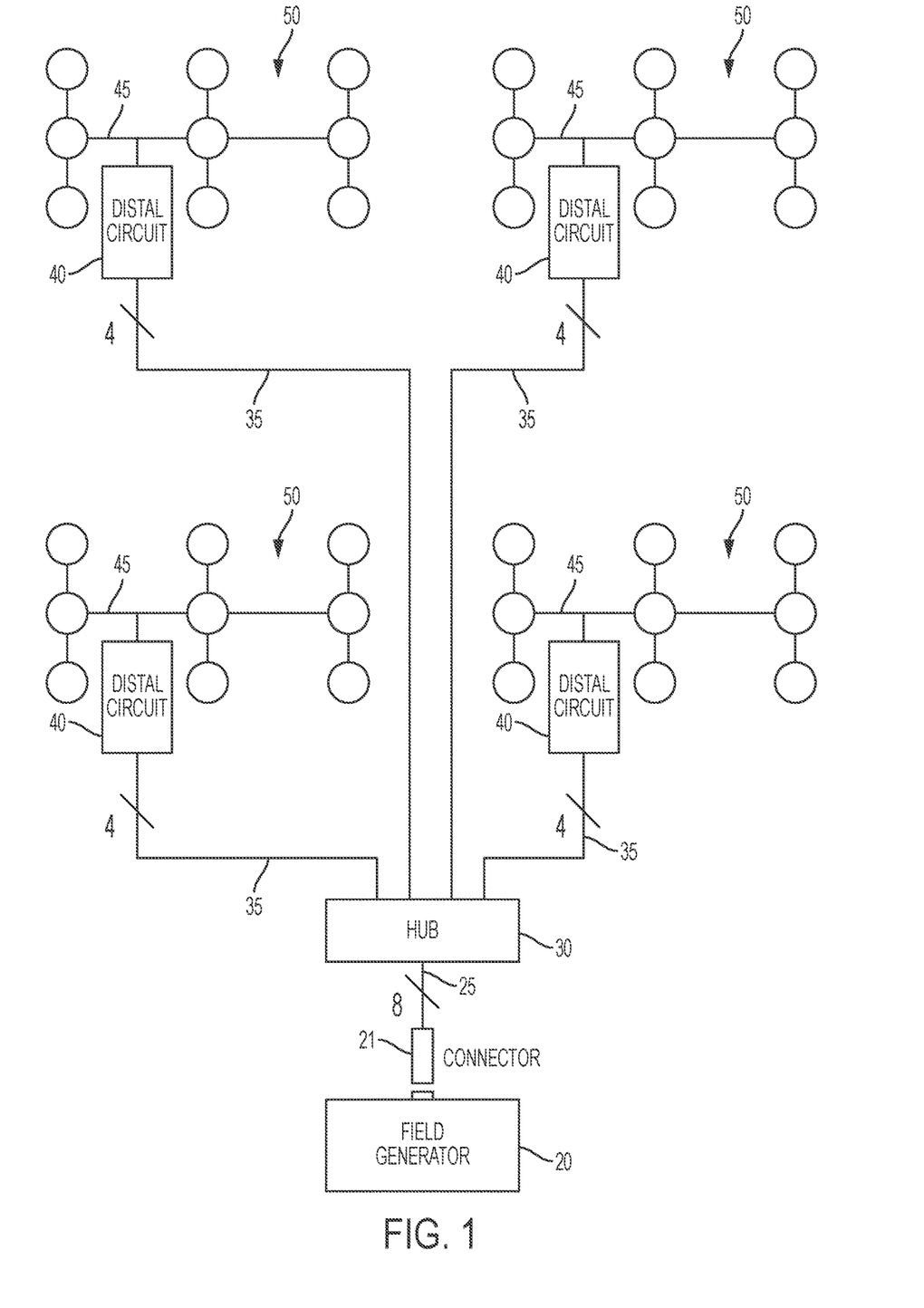
FIG. 1 is a block diagram of a system for measuring the temperature of transducer arrays that are used to apply TTFields to a subject's body.

FIG. 1 is a block diagram of an embodiment that relies on distal circuits 40 positioned in close proximity to each of the four transducer arrays 50 to obtain the temperature readings from the temperature sensors in the transducer arrays 50. Each of the transducer arrays 50 includes a plurality of capacitively coupled electrode elements 52 and a plurality of temperature sensors 54 (both shown in FIGS. 3, 6A, and 6B). The temperature sensors 54 are positioned to detect the temperature at respective electrode elements 52. In some preferred embodiments, the temperature sensors 54 are thermistors.

Returning to FIG. 1, each distal circuit 40 interfaces with the temperature sensors that are incorporated into the respective transducer array 50 to obtain the temperature readings from each temperature sensor. The distal circuit 40 then analog-to-digital converts those temperature readings and forwards the digitized temperature readings along to a central hub 30. The central hub 30 then forwards these digitized temperature readings to the field generator 20 via a serial communication link so that the field generator 20 can determine, based on the temperature readings, if the current to the transducer arrays 50 has to be adjusted.

There are 10 short conductors that extend distally in the wiring 45 beyond the distal circuit 40 into the transducer array 50 itself. Those 10 conductors include 1 conductor for each of the 8 temperature sensors, 1 conductor for the temperature sensors' common ground, and 1 conductor for the TTFields signal (i.e., the AC current for the electrode elements). In some preferred embodiment, the distal circuit 40 is implemented using a single-chip microcontroller or Programmable System on Chip (PSoC) with a built in analog front end and multiplexer. Suitable part numbers for this purpose include the CY8C4124LQI-443. In this case, no other active components are needed in the distal circuit 40. In alternative embodiments, other microcontrollers may be used with either built-in or discrete analog front ends and multiplexers, as will be apparent to persons skilled in the relevant arts. The analog front end and multiplexer obtains temperature readings from the temperature sensors. Those temperature readings are then digitized and transmitted to the central hub 30, preferably via a serial data link. In addition, each distal circuit 40 also has an associated pass-through conductor (51, shown in FIGS. 3 and 6A) for routing the TTFields signal that originated in the field generator 20 to the transducer array 50.

In the FIG. 1 embodiment, each of the four distal circuits 40 is connected to the central hub 30 via a respective cable 35. Notably only 4 conductors are required in each of the cables 35 that run between a distal circuit 40 and the hub 30 (i.e., one for Vcc, one for ground, one for serial data communication, and one for the TTFields signal). The distal circuits 40 therefore dramatically reduce the wire count that is needed to interface with each transducer array 50.

Figure 2:
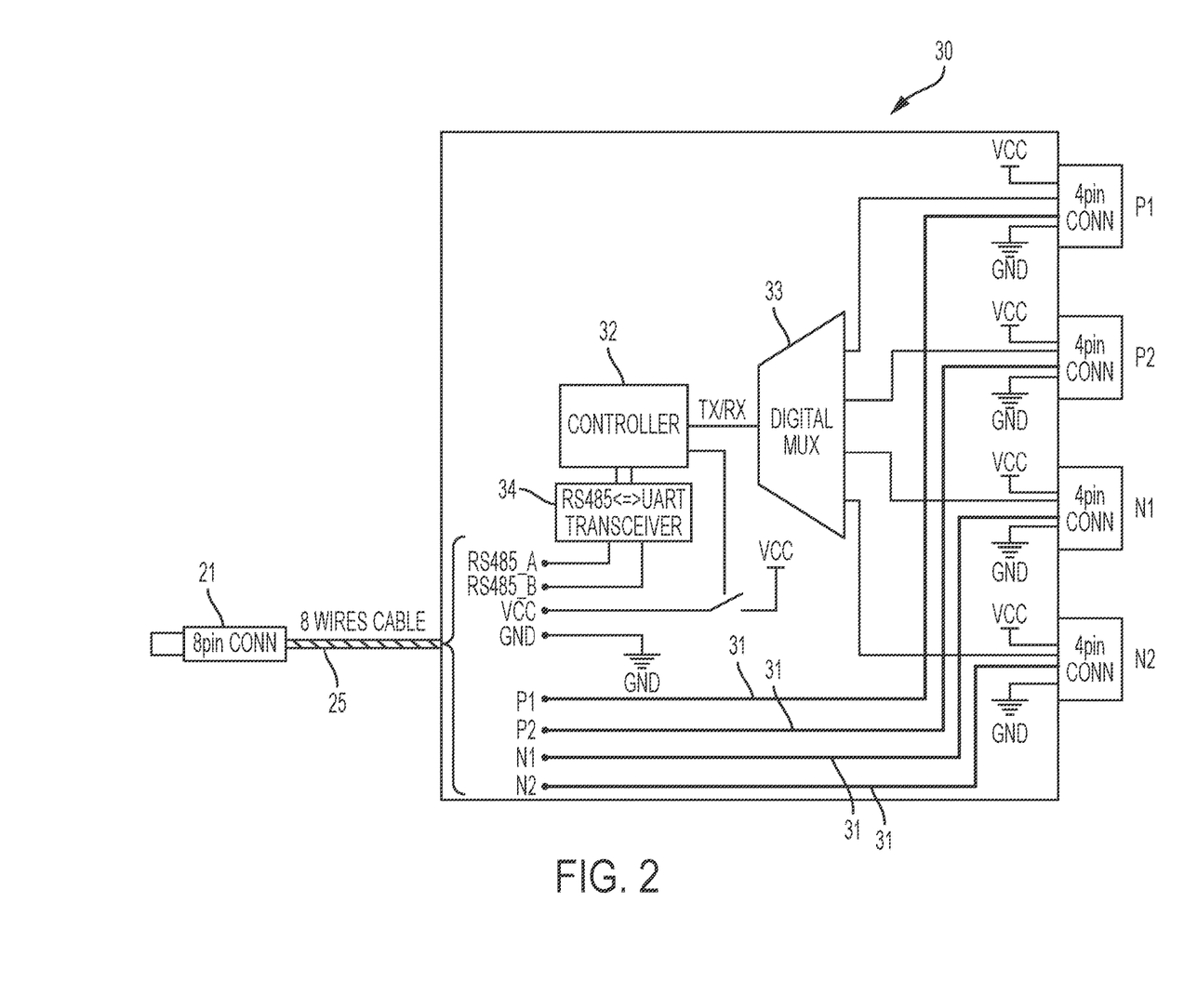
FIG. 2 is a schematic diagram of the hub in the FIG. 1 embodiment.

FIG. 2 is a schematic diagram of a circuit that is suitable for use as the hub 30 depicted in FIG. 1. In general terms, the hub 30 accepts the temperature readings from each of the distal circuits 40 (shown in FIG. 1) and sends those temperature readings along to the field generator 20 (shown in FIG. 1). Any of a wide variety of architectures may be used to accept and send the temperature readings. For example, in the illustrated embodiment, a controller 32 sends a signal to a digital multiplexer 33 that commands the digital multiplexer 33 to select one of the four inputs, which sets the hub 30 up to receive digital data from one of the distal circuits 40 (shown in FIG. 1). After that, the controller 32 accepts all eight temperature readings from the selected input and transmits those temperature readings along to the field generator 20 (shown in FIG. 1) via the transceiver 34. After all the temperature readings from the selected input (i.e., the selected distal circuit) have been transmitted to the field generator, the controller 32 updates the control signal to digital multiplexer 33 and commands the digital multiplexer to select another one of the four inputs (i.e., another distal circuit). The controller 32 then accepts all eight temperature readings from the newly selected input and transmits those temperature readings to the field generator. Corresponding sequences are then performed to obtain eight temperature readings from the third input and eight temperature readings from the fourth input.

In some preferred embodiments, the controller 32, the digital multiplexer 33, and the transceiver 34 may be integrated together into a single chip. In alternative embodiments, the controller 32 and the digital multiplexer 33 are integrated together into a single chip, and a separate transceiver 34 is used. For example, the controller 32 and the digital multiplexer 33 may be implemented using a Cypress CY8C4244LQI-443, and the transceiver 34 may be implemented using a Linear Technology LTC2856CMS8-2#PBF.

The entire sequence of obtaining all of the temperature measurements from each of the four inputs is repeated periodically (e.g., every 1 second, 10 seconds, or 30 seconds) to update the temperature readings that are provided to the field generator 20. The hub 30 communicates with the field generator 20 using any conventional communication technique (e.g., RS485). The hub 30 also includes pass-through conductors 31 that pass the TTField signals directly from the field generator 20 to each of the transducer arrays 50. In one example, the hub 30 communicates with the field generator 20 via an 8-conductor spiral cable 25 (which includes 4 wires for TTFields signal from each array, 1 wire for ground, 1 wire for Vcc to the distal circuits 40 and 2 wires for communication). Notably, this embodiment can be made backwards compatible with previous versions of TTField delivery systems.

In the embodiment described above, two wires are used to implement data communications between the hub 30 and the field generator 20 (i.e., for the temperature data). This may be accomplished, for example, by using one wire to implement communication in each direction. In alternative embodiments, the wire count between the hub 30 and the field generator 20 can be reduced by replacing the two data communication wires in the embodiments described above with a single data wire that implements two-way communication (using a conventional single wire communication protocol).

Figure 3:
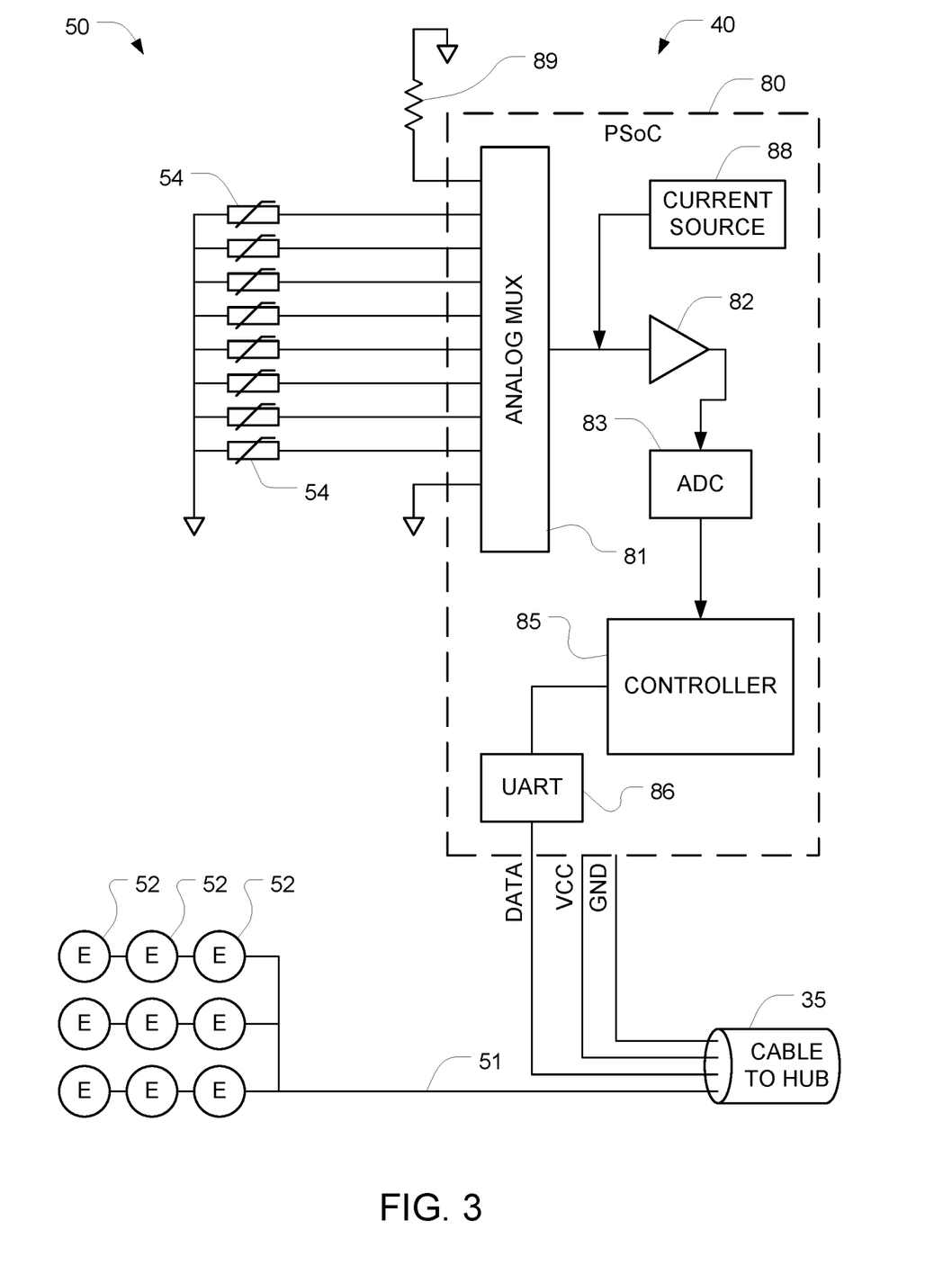
FIG. 3 is a schematic diagram of one of the distal circuits in the FIG. 1 embodiment.

FIG. 3 is a schematic diagram of a circuit for interfacing the hub (shown in FIG. 1) with any given transducer array 50. Each transducer array 50 includes a plurality of capacitively coupled electrode elements 52 and a plurality of temperature sensors 54 positioned to sense temperatures at respective ones of the plurality of electrode elements. In some preferred embodiments, these temperature sensors 54 are thermistors.

An analog multiplexer 81 has an analog output and a plurality of selectable analog inputs, and each of the plurality of the analog inputs is connected to a respective one of the plurality of temperature sensors 54. The second terminal of each temperature sensor 54 goes to a common ground. The output of the analog multiplexer 81 goes to an amplifier 82, preferably with a high input impedance (e.g., an op amp that is configured as a voltage follower). The output of the amplifier 82 is provided to the input of an analog to digital converter 83, and the output of the analog to digital converter is provided to a controller 85.

The controller 85 orchestrates the operation of all of the components within the dashed line 80. The controller 85 sends a command to the analog multiplexer 81 to select one of the temperature sensors 54, in order to obtain a temperature reading from that temperature sensor.

In embodiments where thermistors are used as the temperature sensors 54, temperature readings may be obtained by routing a known current through the thermistor and measuring the voltage that appears across the thermistor. In the illustrated embodiment, this may be achieved using a programmable current source 88, which may be programmed to generate a known current (e.g., 150 µA). The analog multiplexer 81 is bidirectional, so this known current will be routed into whichever thermistor is selected by the analog multiplexer.

Temperature readings from all eight temperature sensors 54 may be obtained using the following procedure. The controller 85 sends a command to the analog multiplexer 81 to select the first thermistor, and configures the current source 88 to generate a known current. Because the first thermistor has been selected, the known current from the current source 88 will flow through the analog multiplexer 81 into the first thermistor. This will cause a voltage to appear across that thermistor. Because the first thermistor is selected, this voltage will appear at the output of the analog multiplexer 81. The amplifier 82 provides this voltage to the input of the analog to digital converter 83. The controller 85 instructs the analog to digital converter 83 to digitize this voltage. The controller 85 obtains this reading from the analog to digital converter 83 and temporarily stores the digitized reading (which corresponds to the first thermistor) in a buffer. This procedure is then repeated, sequentially, for each of the other thermistors until digitized readings from each of the eight thermistors are sitting in the buffer.

In alternative embodiments, not shown, an alternative approach (e.g., the conventional voltage divider approach) for interfacing with the thermistors may be used in place of the constant current approach described above. In other alternative embodiments, a different type of temperature sensor may be used in place of the thermistors described above. Examples include thermocouples, RTDs, and integrated circuit temperature sensors such as the Analog Devices AD590 and the Texas Instruments LM135. Of course, when any of these alternative temperature sensors is used, appropriate modifications to the circuit (which will be apparent to persons skilled in the relevant arts) will be required.

In some embodiments, additional readings may be obtained and used for self-calibration to increase the accuracy of the temperature readings obtained from the thermistors. For example, in the illustrated embodiment, the bottom input of the analog multiplexer 81 is connected to ground, and the top input of the analog multiplexer 81 is connected to a precision resistor 89. In some embodiments, the precision resistor 89 is a 10 kOhm, 0.1% tolerance resistor. Readings from the precision resistor 89 may be obtained using the same procedure described above for obtaining a reading from any one of the thermistors. Obtaining readings from the grounded input of the analog multiplexer 81 is also similar, except that the current source 88 may be deactivated when the grounded input is selected. In these embodiments, the controller 85 temporarily stores the digitized readings from the precision resistor and the grounded input in a buffer (which means that a total of 10 readings are stored in the buffer). These additional readings may ultimately be used to calibrate the readings that were obtained from the thermistors. In some embodiments, this calibration is implemented in the controller 85 itself, prior to transmission of the digital data that corresponds to the temperature readings. In other embodiments, this calibration is implemented in a downstream processor (e.g., the controller 32 in the hub 30, both shown in FIG. 2), in which case the digital data corresponding to the precision resistor (and optionally the grounded input) is transmitted to the downstream processor along with the uncalibrated temperature readings that were obtained from the thermistors.

One suitable approach for performing calibration using the precision resistor 89 is to compare the actual voltage measured across that resistor with the expected voltage based on Ohm's law, the known value of the precision resistor 89, and the expected value of the current being produced by the current source 88. Any deviation between the actual measured voltage and the expected voltage could then be used as a multiplier for subsequent measurements from the thermistors 54.

The controller 85 in the distal circuit 40 communicates with the hub 30 (shown in FIG. 1) via UART 86, and transmits the temperature readings obtained from the temperature sensors 54 to the hub. In some embodiments, the controller 85 may be programmed to operate autonomously, in which case it would automatically collect temperature readings from each of the temperature sensors 54 and store the result in a buffer as described above, and subsequently transmit the contents of the buffer (i.e., readings for each of the eight temperature sensors 54, and optionally the additional readings described above) to the hub.

In alternative embodiments, the controller 85 may be programmed to operate as a slave to a master controller located in the hub. In these embodiments, the controller 85 starts out in a quiescent state, where all it does is monitor incoming commands from the master controller that arrive via the UART 86. Examples of commands that can arrive from the master controller include a "collect samples" command and a "send data" command. When the controller 85 recognizes that a "collect samples" command has arrived, the controller 85 will initiate the procedure described above to obtain temperature readings from each of the eight temperature sensors 54 and store the result in its buffer. When the controller 85 recognizes that a "send data" command has arrived, the controller 85 will execute a procedure that transmits the previously collected temperature readings from the buffer to the hub via the UART 86.

In those embodiments in which the controller 85 operates as a slave to a master controller located in the hub 30, it becomes possible to synchronize the temperature measurements that are obtained from each of the four transducer arrays 50 (shown in FIG. 1). One way to accomplish this would be to have the master controller in the hub 30 send a "collect samples" command to all four controllers 85 either simultaneously or in rapid succession, so that the temperature readings obtained from each of the transducer arrays will be obtained at or near the same time. The temperature readings can then be collected by the hub 30 in batches of eight from each of the four controllers 85.

Most systems that use TTFields to treat tumors switch the direction of the field that is being applied to the tumor periodically (e.g. every second). To minimize noise in the temperature measurements, a small gap in time during which the field is not applied in either direction may be introduced, and the temperature measurements can be made during that gap in time. In some preferred embodiments, the master controller located in the hub 30 synchronizes the timing of the "collect samples" command to all four controllers 85 so that each of the distal circuits 40 will obtain its temperature readings during this gap. In embodiments where the temperature readings are obtained from each of the four transducer arrays simultaneously, this approach can be used to minimize the duration of the gap. For example, if a system requires 100 µs to obtain a single measurement, taking all 32 measurements in sequence (i.e., 4 distal circuits×8 thermistors at each circuit) would take 3.2 ms. In contrast, if each of the four distal circuits operates in parallel, each distal circuit can complete its job in 800 µs, in which case all 32 samples can be obtained in 800 µs. Note that because the "send data" command is not sensitive to noise, that command can be executed while the fields remain on, and is therefore not time-critical.

In some embodiments, some or all of the following components are implemented by a single integrated circuit: analog multiplexer 81, amplifier 82, analog to digital converter 83, controller 85, UART 86, and current source 88. One example of a single integrated circuit that includes all of these functional blocks is the Cypress CY8C4124LQI-443T programmable system on chip (PSoC).

Figure 4A:
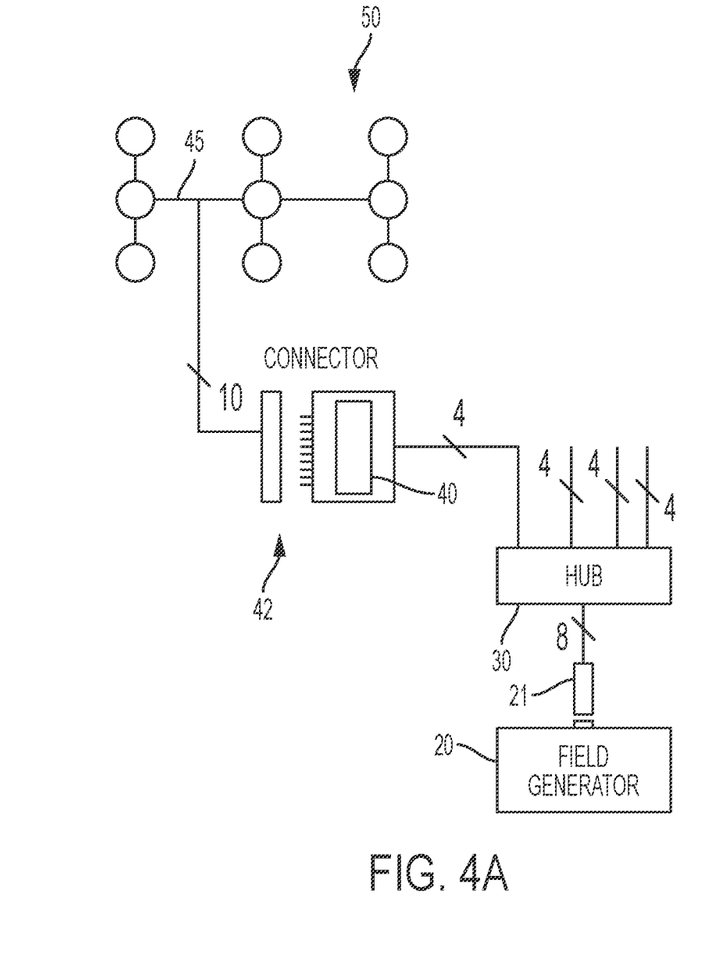
FIG. 4A depicts a first option for connectorizing the FIG. 1 embodiment.
Figure 4B:
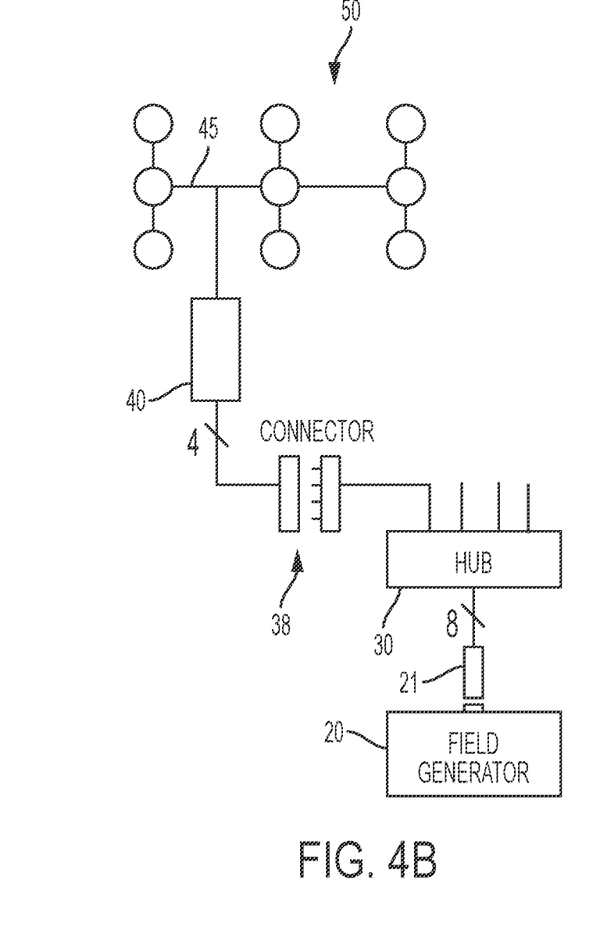
FIG. 4B depicts a second option for connectorizing the FIG. 1 embodiment.

Optionally, a connector may be included in the path between the hub 30 and each of the transducer arrays 50, as shown in FIGS. 4A and 4B for a single transducer array. In the FIG. 4A embodiment, a connector 42 is positioned distally beyond the distal circuit 40; and in the FIG. 4B embodiment, a connector 38 is positioned on the proximal side of the distal circuit 40.

Figure 5A:
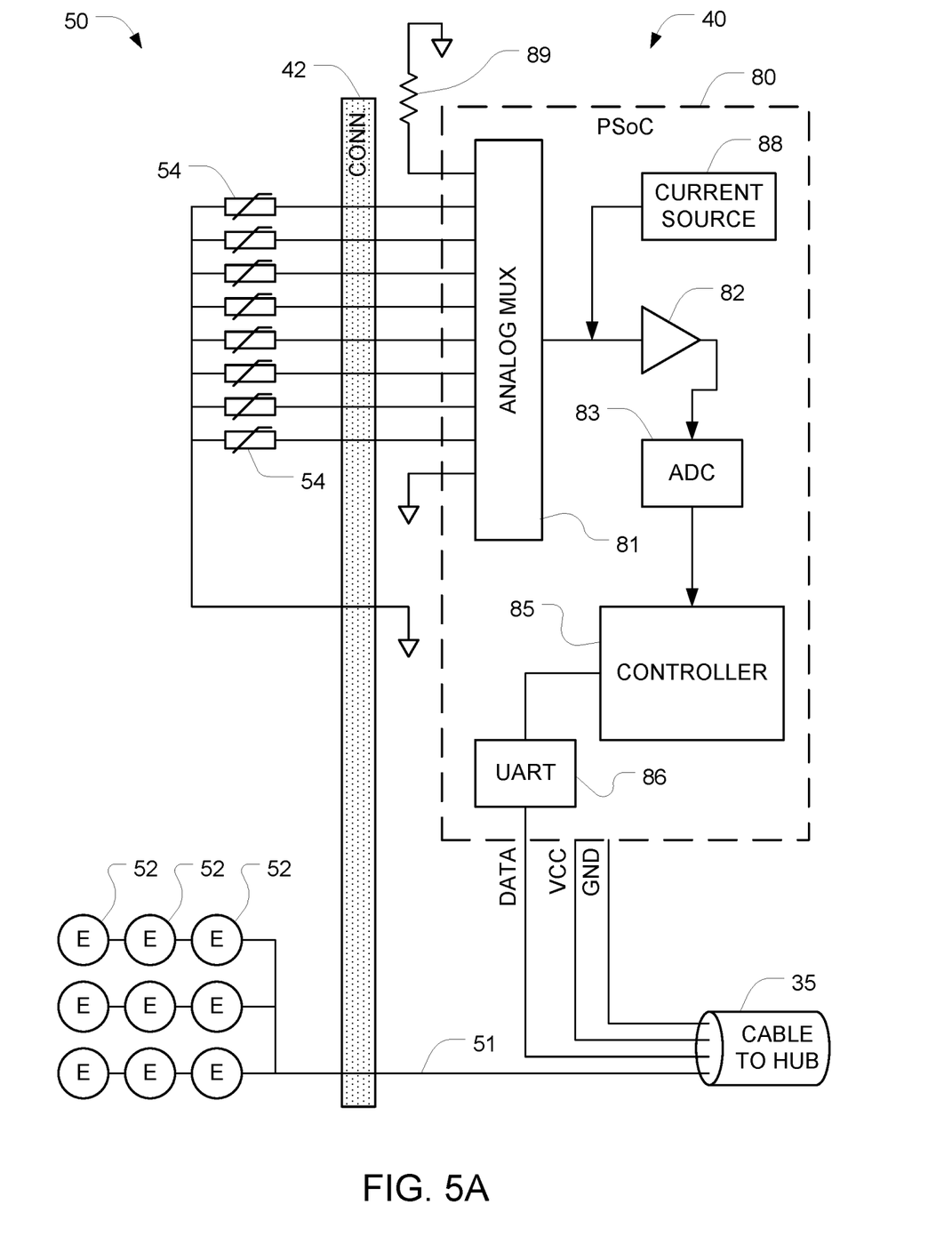
FIG. 5A depicts a detailed view of the connector's position in the FIG. 4A embodiment.

FIG. 5A depicts a more detailed view to show exactly where the connector 42 is positioned in the FIG. 4A embodiment. In this embodiment, the connector 42 is positioned distally beyond the distal circuit 40. Operation of the FIG. 5A embodiment is similar to the operation of the FIG. 3 embodiment discussed above, except that 10 signals traverse the connector 42: one for the AC current that goes to the electrode elements 52; one for each of the eight temperature sensors 54 (for a subtotal of eight); and one for a common ground that is used for all of the eight temperature sensors 54.

Figure 5B:
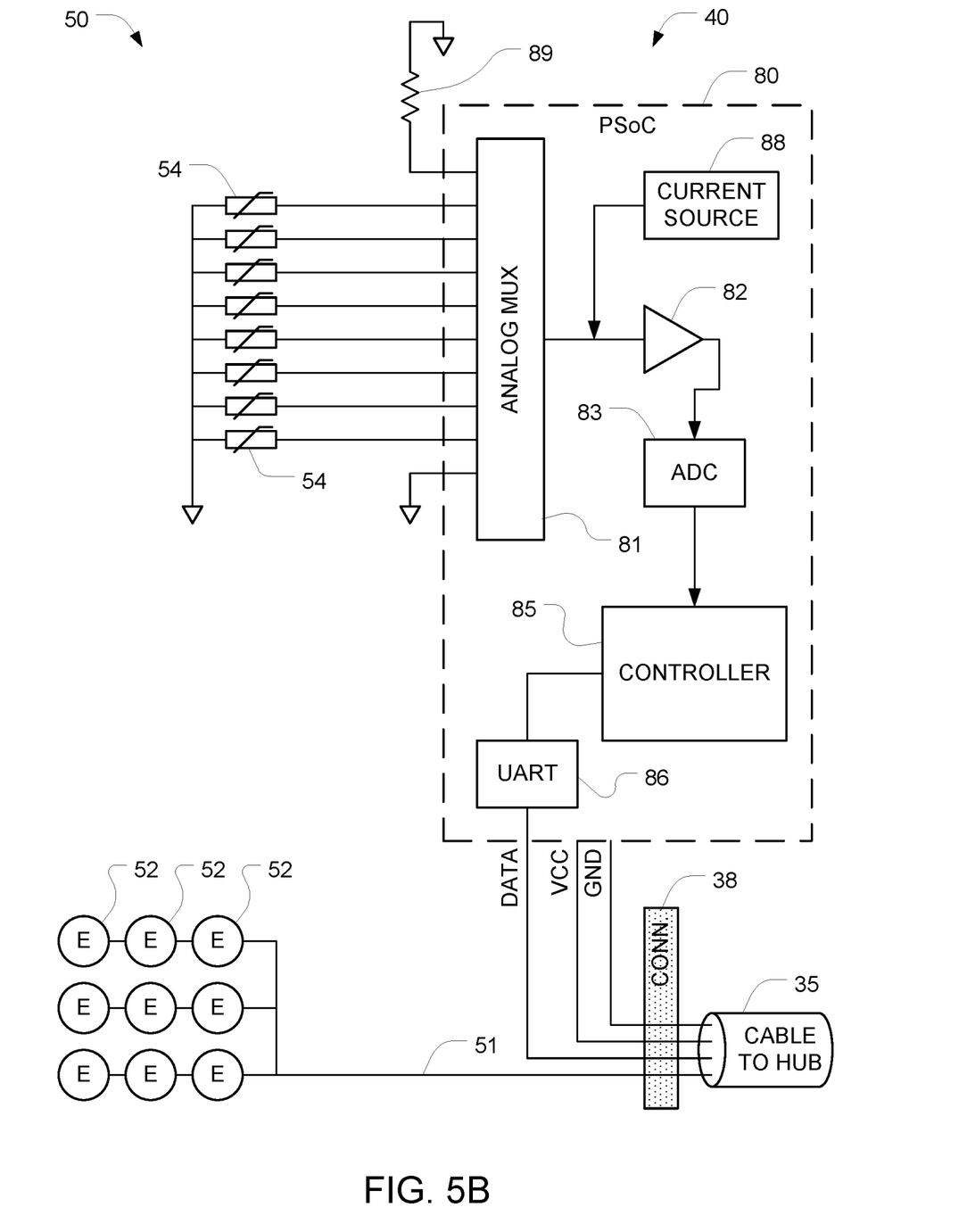
FIG. 5B depicts a detailed view of the connector's position in the FIG. 4B embodiment.

FIG. 5B depicts a more detailed view to show exactly where the connector 38 is positioned in the FIG. 4B embodiment. In this embodiment, the connector 38 is positioned on the proximal side of the distal circuit 40. Operation of the FIG. 5B embodiment is similar to the operation of the FIG. 3 embodiment discussed above, except that 4 signals traverse the connector 38: one for the AC current that goes to the electrode elements 52, one for data that travels between the UART 86 and the hub; one for power to the distal circuit 40, and one for ground for the distal circuit 40.

Figure 6A:
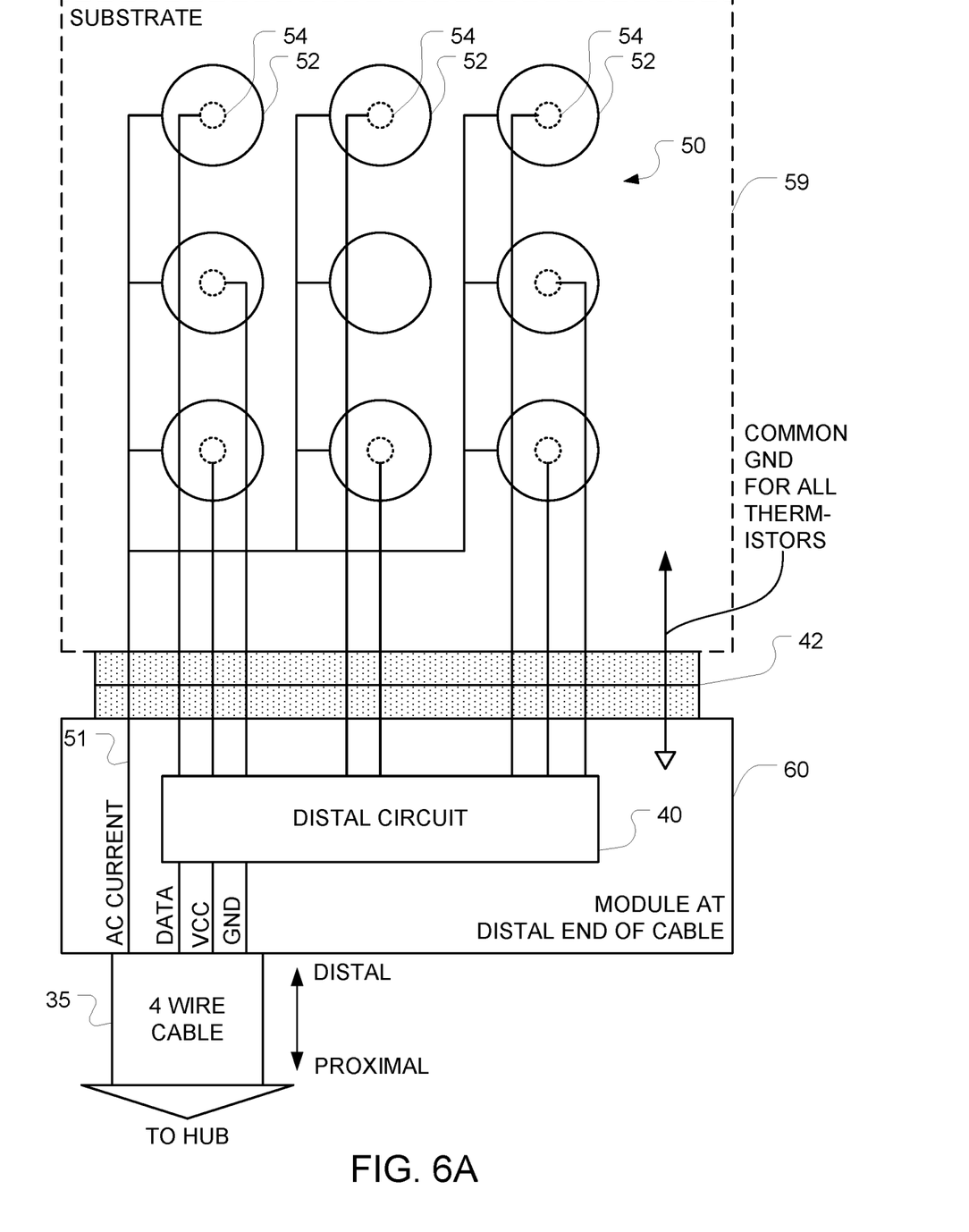
FIG. 6A depicts the mechanical layout for the FIG. 4A embodiment.

FIG. 6A depicts the mechanical layout for the FIG. 4A/5A embodiment. In this embodiment, a substrate 59 supports a plurality of capacitively coupled electrode elements 52. The electrode elements 52 are configured for placement against the subject's body, and the substrate 59 is configured to hold the plurality of electrode elements 52 against the subject's body. A plurality of temperature sensors 54 are positioned adjacent to and/or beneath respective ones of the electrode elements 52 so that the temperature sensors 54 can sense the temperatures of those electrode elements.

A cable 35 has a proximal end and a distal end. This cable 35 includes (i) a conductor 51 that permits AC current to flow between the proximal end of the cable and the distal end of the cable and (ii) a data path configured to carry the digital data corresponding to the plurality of temperature readings (which originates in the distal circuit 40) from the distal end of the cable to the proximal end of the cable (i.e., in the direction of the hub).

A module 60 is mounted (either directly or through intervening components) to the distal end of the cable 35. The distal circuit 40 is mounted in this module 60. In some embodiments, power and ground for the distal circuit 40 is provided through the cable 35. A first half of a connector 42 is provided at the distal end of the module 60, and the second half of the connector 42 is provided on the substrate 59. The first half of the connector 42 mates with the second half of the connector 42 so that electrical signals can pass through both halves of the connector 42. When both halves of the connector 42 are mated, signals from the eight thermistors 54 will travel through wiring on the substrate 59, through the connector 42, and into the distal circuit 40. This distal circuit 40 includes the analog multiplexer, the analog to digital converter, and the controller (described above in connection with FIG. 3). In addition, a common ground signal for all the thermistors 54 is provided through the connector 42. A path for the AC current for the electrode elements 52 is also provided through the connector 42. This path continues through appropriate wiring on the substrate 59 so that the plurality of electrode elements 52 will be electrically connected to a corresponding conductor of the cable 35.

Figure 6B:
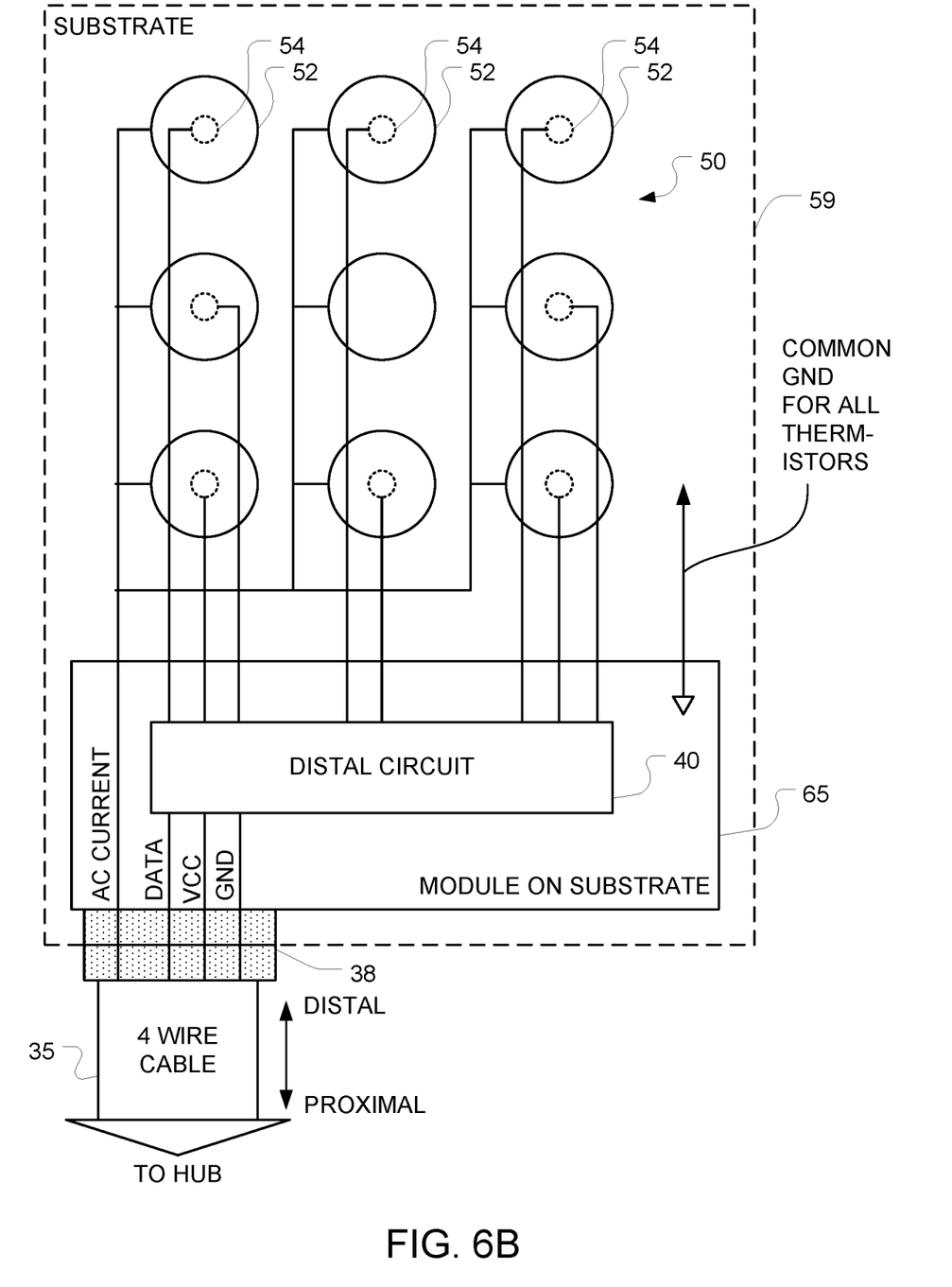
FIG. 6B depicts the mechanical layout for the FIG. 4B embodiment.

FIG. 6B depicts the mechanical layout for the FIG. 4B/5B embodiment. In this embodiment, a substrate 59 supports a plurality of capacitively coupled electrode elements 52. The electrode elements 52 are configured for placement against the subject's body, and the substrate 59 is configured to hold the plurality of electrode elements 52 against the subject's body. A plurality of temperature sensors 54 are positioned adjacent to and/or beneath respective ones of the electrode elements 52 so that the temperature sensors 54 can sense the temperatures of those electrode elements.

A cable 35 has a proximal end and a distal end. This cable 35 includes (i) a conductor 51 that permits AC current to flow between the proximal end of the cable and the distal end of the cable and (ii) a data path configured to carry the digital data corresponding to the plurality of temperature readings (which originates in the distal circuit 40) from the distal end of the cable to the proximal end of the cable (i.e., in the direction of the hub).

A module 65 is mounted (either directly or through intervening components) to the substrate 59. The distal circuit 40 is mounted in this module 65. In some embodiments, power and ground for the distal circuit 40 are provided through the cable 35. A first half of a connector 38 is provided at the distal end of the cable 35, and the second half of the connector 38 is provided on the substrate 59. The first half of the connector 38 mates with the second half of the connector 38 so that electrical signals can pass through both halves of the connector 38. When both halves of the connector 38 are mated, signals from the cable 35 will travel through the connector 38, and into the distal circuit 40. This distal circuit 40 includes the analog multiplexer, the analog to digital converter, and the controller (described above in connection with FIG. 3). In addition, a path for the AC current for the electrode elements 52 is also provided through the connector 38. This path continues through appropriate wiring on the substrate 59 so that the plurality of electrode elements 52 will be electrically connected to a corresponding conductor of the cable 35.

The connectorized design depicted in FIGS. 4-6 provides a significant advantage over non-connectorized embodiments in that the patient or caregiver can attach the transducer arrays 50 to the patient's skin without being hindered by the presence of cables. In these embodiments, the cables 35 are preferably disconnected from the substrates 59 when the transducer arrays 50 are initially placed on the patient's body. Only after the transducer arrays 50 are affixed in their desired positions are the cables 35 connected to the transducer arrays 50 via the connectors 38 or 42. The connectors are preferably waterproof to prevent moisture (e.g., perspiration, showers, etc.) from interfering with the electric circuitry.

Note that the FIG. 4A/5A/6A embodiment has an advantage over both the non-connectorized FIG. 1 embodiment and the FIG. 4B/5B/6B embodiment because the transducer arrays 50 are preferably sterilized before use. Sterilization is ordinarily performed using either radiation or gas. Since radiation can interfere with electronics, assemblies in which the distal circuit 40 cannot be disconnected from the transducer arrays 50 can only be sterilized with gas. On the other hand, if the distal circuit 40 is located on the proximal side of the connector 42 (as it is in the FIG. 4A/5A/6A embodiment), the portion that includes the distal circuit 40 will not require sterilization. This permits sterilization of the transducer arrays 50 in the FIG. 4A/5A/6A embodiment to be performed using either gas or radiation without risk of damage to the distal circuit 40.

Each of the configurations described above has significant advantages over the prior art because only 4 conductors are needed in each of the cables 35 that interface with each transducer array 50. Furthermore, because only 4 conductors are required, the cables 35 that extend distally beyond the hub 30 can be made thinner and smaller than the prior art cables. This makes it easier to mount the hub 30 on a portion of the body that is adjacent to the transducer arrays 50, and to make small and lightweight interconnections between the hub 30 and the transducer arrays 50. For example, when the transducer arrays 50 are affixed to the patient's scalp, it becomes possible to mount the hub 30 on the patient's head in the vicinity of the transducer arrays 50 without discomfort to the patient. In these embodiments, shorter cables 35 (e.g., less than 25 cm or even less than 10 cm) are preferably used to interconnect the hub 30 with both the transducer arrays 50 and the distal circuit 40.

The configurations described herein can advantageously reduce tangling of the cables that lead to the transducer arrays 50, reduce the number of times that the cables will interfere with patients' everyday activities, reduce the overall cumbersomeness of the system, improve patient comfort, and improve maneuverability of the electrodes when they are affixed to the patient's body.

Returning to FIG. 1, a display unit (not shown) may be added to the system. This display unit may be used to display information that the device provides to the patient including but not limited to device status (e.g., on/standby), error indications, status of battery charge, compliance metrics, etc. The display unit may be mounted at any point along the cable 25 between the hub 30 and the field generator 20. In alternative embodiments, the display unit 22 may be mounted to the hub 30 itself.

In some alternative embodiments, the wires that provide power and ground to the distal circuit 40 can also be eliminated by diverting some of the energy from the TTFields signal (which is delivered via pass-through conductors) using a coil, storing that energy in a capacitor adjacent to the distal circuit 40, and powering the distal circuit 40 using the stored energy. It is even possible to implement a one-wire communication protocol that transmits the temperature data over the TTFields signal wire. In such a configuration, the data communication signals and power for the distal circuits (Vcc) could all be removed from the cable that runs to the transducer array 50. If all of these wire reduction techniques are implemented, only two wires will be needed between the hub 30 and each transducer array 50 (i.e., 1 for the TTField signal and 1 for ground). And the total number of wires that run back from the four transducer arrays 50 to the field generator 20 would be reduced to 5 (i.e., 1 for a common ground and a total of 4 for the TTField signals).

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for use together with a AC signal generator for imposing electric fields through a target region in a subject's body, the apparatus comprising:
    a first subassembly inluding
        a plurality of capacitively coupled electrode elements configured for placement against the subject's body,
        a substrate configured to hold the plurality of capacitively coupled electrode elements against the subject's body, a plurality of temperature sensors positioned to sense temperatures at respective ones of the plurality of capacitively coupled electrode elements, each of the temperature sensors having a respective output, and a first connector having a first terminal that is electrically connected to the plurality of capacitively coupled electrode elements and a plurality of second terminals, each of which is electrically connected to a respective output of the plurality of temperature sensors; and a second subassembly inluding a second connector configured to removably mate with the first connector, the second connector having a first terminal configured to removably mate with the first terminal of the first connector and a plurality of second terminals, each of which is configured to removably mate with a corresponding second terminal of the first connector, an analog multiplexer having an analog output and a plurality of selectable analog inputs, wherein each of the plurality of selectable analog inputs is operatively connected to a respective one of the second terminals of the second connector, an analog to digital converter configured to digitize signals arriving from the analog output, a controller configured to, when the first connector and the second connector are mated,(a) sequentially select each of the plurality of selectable analog inputs, (b) sequentially obtain, from the analog to digital converter, a plurality of temperature readings, each of the plurality of temperature readings corresponding to a respective one of the plurality of temperature sensors, and (c) transmit digital data corresponding to the plurality of temperature readings, and a cable with multiple conductors and having a proximal end and a distal end, wherein the cable includes (i) a first conductor that permits AC current to flow between the proximal end of the cable and the first terminal of the second connector and (ii) a data path configured to carry the digital data transmitted by the controller from the distal end of the cable to the proximal end of the cable wherein the analog multiplexer, the analog to digital converter, and the controller are mounted to the distal end of the cable.

2. The apparatus of claim 1, wherein the plurality of temperature sensors comprises a plurality of thermistors.

3. The apparatus of claim 1, wherein the cable has a length of 25 cm or less.

4. The apparatus of claim 1, wherein the cable has a length of 10 cm or less.

5. The apparatus of claim 1, further comprising:

a precision resistor, wherein the analog multiplexer has an additional selectable analog input that is operatively connected to the precision resistor, and wherein the controller is further configured to (d) select the additional selectable analog input, (e) obtain, from the analog to digital converter, an additional reading that corresponds to the precision resistor, and (f) transmit digital data corresponding to the additional reading.

6. The apparatus of claim 1, further comprising:

a precision resistor, wherein the analog multiplexer has an additional selectable analog input that is operatively connected to the precision resistor, and wherein the controller is further configured to (d) select the additional selectable analog input, (e) obtain, from the analog to digital converter, an additional reading that corresponds to the precision resistor, and (f) calibrate, based on the additional reading, each of the plurality of temperature readings prior to transmission of the corresponding digital data.

7. The apparatus of claim 1, wherein the cable uses a single conductor to provide the data path that carries the transmitted digital data from the distal end of the cable to the proximal end of the cable.

8. The apparatus of claim 1, wherein the cable uses a single conductor to provide the data path that carries the transmitted digital data from the distal end of the cable to the proximal end of the cable, a single conductor for providing power to the controller, and a single conductor for ground.

9. The apparatus of claim 1, wherein energy arriving via the first conductor in the cable is used to power the controller.

10. An apparatus for use together with an AC signal generator for imposing electric fields through a target region in a subject's body, the apparatus comprising:

a hub configured to accept digital data corresponding to first, second, third, and fourth pluralities of temperature readings and output digital data corresponding to the first, second, third, and fourth pluralities of temperature readings to the AC signal generator, wherein the hub includes first, second, third, and fourth conductors configured to route current from the AC signal generator to positions that are located distally beyond the hub;

a first plurality of capacitively coupled electrode elements configured for placement against the subject's body at a first position;

a first substrate configured to hold the first plurality of electrode elements against the subject's body at the first position;

a first plurality of temperature sensors positioned to sense temperatures at respective ones of the first plurality of electrode elements;

a first analog multiplexer having a first analog output and a first plurality of selectable analog inputs, wherein each of the first plurality of analog inputs is operatively connected to a respective one of the first plurality of temperature sensors;

a first analog to digital converter configured to digitize signals arriving from the first analog output;

a first controller configured to (a) sequentially select each of the first plurality of analog inputs, (b) sequentially obtain, from the first analog to digital converter, a first plurality of temperature readings, each of the first plurality of temperature readings corresponding to a respective one of the first plurality of temperature sensors, and (c) transmit first digital data corresponding to the first plurality of temperature readings to the hub;

a first cable arranged to route current arriving via the first conductor in the hub to the first plurality of electrode elements, and to route the first digital data from the first controller to the hub;

a second plurality of capacitively coupled electrode elements configured for placement against the subject's body at a second position;

a second substrate configured to hold the second plurality of electrode elements against the subject's body at the second position;

a second plurality of temperature sensors positioned to sense temperatures at respective ones of the second plurality of electrode elements;

a second analog multiplexer having a second analog output and a second plurality of selectable analog inputs, wherein each of the second plurality of analog inputs is operatively connected to a respective one of the second plurality of temperature sensors;
a second analog to digital converter configured to digitize signals arriving from the second analog output;
a second controller configured to (a) sequentially select each of the second plurality of analog inputs, (b) sequentially obtain, from the second analog to digital converter, a second plurality of temperature readings, each of the second plurality of temperature readings corresponding to a respective one of the second plurality of temperature sensors, and (c) transmit second digital data corresponding to the second plurality of temperature readings to the hub;
a second cable arranged to route current arriving via the second conductor in the hub to the second plurality of electrode elements, and to route the second digital data from the second controller to the hub;
a third plurality of capacitively coupled electrode elements configured for placement against the subject's body at a third position;
a third substrate configured to hold the third plurality of electrode elements against the subject's body at the third position;
a third plurality of temperature sensors positioned to sense temperatures at respective ones of the third plurality of electrode elements;
a third analog multiplexer having a third analog output and a third plurality of selectable analog inputs, wherein each of the third plurality of analog inputs is operatively connected to a respective one of the third plurality of temperature sensors;
a third analog to digital converter configured to digitize signals arriving from the third analog output;
a third controller configured to (a) sequentially select each of the third plurality of analog inputs, (b) sequentially obtain, from the third analog to digital converter, a third plurality of temperature readings, each of the third plurality of temperature readings corresponding to a respective one of the third plurality of temperature sensors, and (c) transmit third digital data corresponding to the third plurality of temperature readings to the hub;
a third cable arranged to route current arriving via the third conductor in the hub to the third plurality of electrode elements, and to route the third digital data from the third controller to the hub;
a fourth plurality of capacitively coupled electrode elements configured for placement against the subject's body at a fourth position;
a fourth substrate configured to hold the fourth plurality of electrode elements against the subject's body at the fourth position;
a fourth plurality of temperature sensors positioned to sense temperatures at respective ones of the fourth plurality of electrode elements;
a fourth analog multiplexer having a fourth analog output and a fourth plurality of selectable analog inputs, wherein each of the fourth plurality of analog inputs is operatively connected to a respective one of the fourth plurality of temperature sensors;
a fourth analog to digital converter configured to digitize signals arriving from the fourth analog output;
a fourth controller configured to (a) sequentially select each of the fourth plurality of analog inputs, (b) sequentially obtain, from the fourth analog to digital converter, a fourth plurality of temperature readings, each of the fourth plurality of temperature readings corresponding to a respective one of the fourth plurality of temperature sensors, and (c) transmit fourth digital data corresponding to the fourth plurality of temperature readings to the hub; and
a fourth cable arranged to route current arriving via the fourth conductor in the hub to the fourth plurality of electrode elements, and to route the fourth digital data from the fourth controller to the hub.

11. The apparatus of claim 10, wherein the first, second, third, and fourth controllers are synchronized so that the first, second, third, and fourth pluralities of temperature readings are obtained simultaneously.

12. The apparatus of claim 10, wherein the first, second, third, and fourth controllers are synchronized so that at least a portion of the first, second, third, and fourth pluralities of temperature readings are obtained simultaneously.

13. The apparatus of claim 10, further comprising:
a first precision resistor;
a second precision resistor;
a third precision resistor; and
a fourth precision resistor,
wherein the first analog multiplexer has a first additional selectable analog input that is operatively connected to the first precision resistor,
wherein the first controller is further configured to (d) select the first additional analog input, (e) obtain, from the first analog to digital converter, a first additional reading that corresponds to the first precision resistor, and (f) transmit digital data corresponding to the first additional reading to the hub,
wherein the second analog multiplexer has a second additional selectable analog input that is operatively connected to the second precision resistor,
wherein the second controller is further configured to (d) select the second additional analog input, (e) obtain, from the second analog to digital converter, a second additional reading that corresponds to the second precision resistor, and (f) transmit digital data corresponding to the second additional reading to the hub,
wherein the third analog multiplexer has a third additional selectable analog input that is operatively connected to the third precision resistor,
wherein the third controller is further configured to (d) select the third additional analog input, (e) obtain, from the third analog to digital converter, a third additional reading that corresponds to the third precision resistor, and (f) transmit digital data corresponding to the third additional reading to the hub,
wherein the fourth analog multiplexer has a fourth additional selectable analog input that is operatively connected to the fourth precision resistor, and
wherein the fourth controller is further configured to (d) select the fourth additional analog input, (e) obtain, from the fourth analog to digital converter, a fourth additional reading that corresponds to the fourth precision resistor, and (f) transmit digital data corresponding to the fourth additional reading to the hub.

14. The apparatus of claim 13, wherein the hub is further configured to:
calibrate, based on the first additional reading, each of the plurality of first temperature readings,
calibrate, based on the second additional reading, each of the plurality of second temperature readings,
calibrate, based on the third additional reading, each of the plurality of third temperature readings, and calibrate, based on the fourth additional reading, each of the plurality of fourth temperature readings.

15. The apparatus of claim 10, further comprising:
a first precision resistor;
a second precision resistor;
a third precision resistor; and
a fourth precision resistor,
wherein the first analog multiplexer has a first additional selectable analog input that is operatively connected to the first precision resistor, and
wherein the first controller is further configured to (d) select the first additional analog input, (e) obtain, from the first analog to digital converter, a first additional reading that corresponds to the first precision resistor, and (f) calibrate, based on the first additional reading, each of the plurality of first temperature readings prior to transmission of the corresponding digital data to the hub,
wherein the second analog multiplexer has a second additional selectable analog input that is operatively connected to the second precision resistor,
wherein the second controller is further configured to (d) select the second additional analog input, (e) obtain, from the second analog to digital converter, a second additional reading that corresponds to the second precision resistor, and (f) calibrate, based on the second additional reading, each of the plurality of second temperature readings prior to transmission of the corresponding digital data to the hub,
wherein the third analog multiplexer has a third additional selectable analog input that is operatively connected to the third precision resistor,
wherein the third controller is further configured to (d) select the third additional analog input, (e) obtain, from the third analog to digital converter, a third additional reading that corresponds to the third precision resistor, and (f) calibrate, based on the third additional reading, each of the plurality of third temperature readings prior to transmission of the corresponding digital data to the hub,
wherein the fourth analog multiplexer has a fourth additional selectable analog input that is operatively connected to the fourth precision resistor, and
wherein the fourth controller is further configured to (d) select the fourth additional analog input, (e) obtain, from the fourth analog to digital converter, a fourth additional reading that corresponds to the fourth precision resistor, and (f) calibrate, based on the fourth additional reading, each of the plurality of fourth temperature readings prior to transmission of the corresponding digital data to the hub.

16. The apparatus of claim 10, further comprising:
a first connector disposed between the first controller and the hub;
a second connector disposed between the second controller and the hub;
a third connector disposed between the third controller and the hub; and
a fourth connector disposed between the fourth controller and the hub.

17. The apparatus of claim 10, further comprising:
a first connector disposed between the first plurality of temperature sensors and the first plurality of analog inputs;
a second connector disposed between the second plurality of temperature sensors and the second plurality of analog inputs;
a third connector disposed between the third plurality of temperature sensors and the third plurality of analog inputs; and
a fourth connector disposed between the fourth plurality of temperature sensors and the fourth plurality of analog inputs.

18. The apparatus of claim 10, wherein
the first cable uses a single conductor for routing current arriving via the first conductor in the hub to the first plurality of electrode elements, and a single conductor for transferring digital data between the first controller and the hub,
the second cable uses a single conductor for routing current arriving via the second conductor in the hub to the second plurality of electrode elements, and a single conductor for transferring digital data between the second controller and the hub,
the third cable uses a single conductor for routing current arriving via the third conductor in the hub to the third plurality of electrode elements, and a single conductor for transferring digital data between the third controller and the hub, and
the fourth cable uses a single conductor for routing current arriving via the fourth conductor in the hub to the fourth plurality of electrode elements, and a single conductor for transferring digital data between the fourth controller and the hub.

19. The apparatus of claim 10, wherein
the first cable uses a single conductor for routing current arriving via the first conductor in the hub to the first plurality of electrode elements, a single conductor for transferring digital data between the first controller and the hub, a single conductor for providing power to the first controller, and a single conductor for ground,
the second cable uses a single conductor for routing current arriving via the second conductor in the hub to the second plurality of electrode elements, a single conductor for transferring digital data between the second controller and the hub, a single conductor for providing power to the second controller, and a single conductor for ground,
the third cable uses a single conductor for routing current arriving via the third conductor in the hub to the third plurality of electrode elements, a single conductor for transferring digital data between the third controller and the hub, a single conductor for providing power to the third controller, and a single conductor for ground, and
the fourth cable uses a single conductor for routing current arriving via the fourth conductor in the hub to the fourth plurality of electrode elements, a single conductor for transferring digital data between the fourth controller and the hub, a single conductor for providing power to the fourth controller, and a single conductor for ground.

20. The apparatus of claim 10, wherein energy arriving via the first, second, third, and fourth conductors in the hub is used to power the first, second, third, and fourth controllers, respectively.

* * * * *